United States Patent [19]

Kozulic

[11] Patent Number: 5,541,255
[45] Date of Patent: Jul. 30, 1996

[54] CROSS-LINKED LINEAR POLYSACCHARIDE POLYMERS AS GELS FOR ELECTROPHORESIS

[75] Inventor: Branko Kozulic, Zurich, Switzerland

[73] Assignee: Guest Elchrom Scientific, Ltd., Cham, Switzerland

[21] Appl. No.: 268,436

[22] Filed: Jun. 30, 1994

Related U.S. Application Data

[62] Division of Ser. No. 998,299, Dec. 30, 1992, Pat. No. 5,371,208.

[51] Int. Cl.$^6$ ............................ C08L 5/00; C08L 1/28
[52] U.S. Cl. ........................ 525/54.3; 536/84; 536/87; 536/123.1
[58] Field of Search ............................ 536/1.11, 51, 84, 536/102, 112, 114, 123.12; 524/27, 35, 44, 47, 54; 525/54.3, 54.31

[56] References Cited

U.S. PATENT DOCUMENTS

| | | | |
|---|---|---|---|
| 3,507,851 | 4/1970 | Ghetie et al. | 536/54 |
| 3,850,798 | 11/1974 | Sjoquist | 530/350 |
| 3,860,573 | 1/1975 | Honamen et al. | 536/114 |
| 3,956,272 | 5/1976 | Tixier | 536/55.1 |
| 3,956,273 | 5/1976 | Guiseley | 536/120 |
| 3,959,251 | 5/1976 | Porath et al. | 536/123.1 |
| 3,995,018 | 11/1976 | Sjoquist | 435/7.92 |
| 4,094,832 | 6/1978 | Soderberg | 526/238.22 |
| 4,290,911 | 9/1981 | Cook et al. | 252/315.3 |
| 4,312,739 | 1/1982 | Hansson et al. | 204/299 |
| 4,319,975 | 3/1982 | Cook | 204/182.8 |
| 4,321,121 | 3/1982 | Gurske | 204/182.8 |
| 4,393,140 | 7/1983 | Schutt | 435/226 |
| 4,421,650 | 12/1983 | Nagasawa et al. | 210/635 |
| 4,459,358 | 7/1984 | Berke | 436/170 |
| 4,504,641 | 3/1985 | Nochumsay | 526/238.2 |
| 4,693,985 | 9/1987 | Degan et al. | 436/531 |
| 4,861,705 | 8/1989 | Margel | 435/2 |
| 4,930,893 | 6/1990 | Mahian | 356/344 |
| 5,009,759 | 4/1991 | Serwer et al. | 204/182.8 |
| 5,037,527 | 8/1991 | Hayashi et al. | 204/435 |
| 5,202,007 | 4/1993 | Kozulic | 204/182.8 |

*Primary Examiner*—Jeffrey Mullis
*Attorney, Agent, or Firm*—Nikaido, Marmelstein, Murray & Oram, LLP

[57] ABSTRACT

A bed of water insoluble, transparent, cross-linked gel, suitable for use in electrophoresis, is formed by dissolving a polysaccharide, including at least one linear polysaccharide such as agarose or hydroxyethyl cellulose, in a suitable solvent, such as water; adding a cross-linking agent, which is not charged nor becomes charged upon contact with water in a pH range of 2 to 11, to the solution; and incubating this mixture in a quiescent state to substantially simultaneously react the polysaccharide and the cross-linking agent and to gel the reaction product into a bed. The polysaccharide is at least one linear polysaccharides, but that linear polysaccharide may also be admixed with other linear polysaccharides and/or at least one non-linear polysaccharide. Synthetic organic polymers may also be admixed in the cross-linking reaction mixture. The polysaccharide, and/or other polymers in the cross-linking reaction mixture may be charged but are preferably uncharged, but if charged, the charge must be low enough so that the charge of the resulting gel, if any, will not interfere with the use of the gel to support an electrophoresis process. When the linear polysaccharide is agarose, the gel has improved elasticity, transparency, and, when the gelled cross-linked product is used to support electrophoresis, improved resolution of small DNA molecules as compared to the results achieved by using an agarose polymer which has not been cross-linked according to this invention.

21 Claims, 6 Drawing Sheets

CROSS-LINKED LINEAR POLYSACCHARIDE POLYMERS AS GELS FOR ELECTROPHORESIS

This is a division of application Ser. No. 07/998,299, filed Dec. 30, 1992, now U.S. Pat. No. 5,371,208.

FIELD OF THE INVENTION

This invention relates to novel gels and the use of these gels as a matrix for electrophoretic separation of molecules.

BACKGROUND OF THE INVENTION

Electrophoresis is a process for separation of charged species based on different mobilities of these species in electric field. The mobilities depend on electrophoresis medium, electric field strength and characteristics of ions themselves, including net surface charge, size and shape. Small species, like metal ions, as well as large species such as viruses have been separated by electrophoretic techniques. However, electrophoresis is currently used mostly for separation of biological macromolecules, including proteins, nucleic acids and their derivatives. The process is usually carried out by forcing the molecules to migrate through an aqueous gel as the electrophoresis medium. The gels may be composed of natural or synthetic polymers. Agarose is the most widely used natural material and polyacrylamide gels represent the most common synthetic matrix. The gels are run essentially in two types of electrophoretic units, including vertical and horizontal ones. In horizontal units the contact between the electrodes and the gel may be established directly or by means of wicks. Alternatively, the gel may be immersed in a buffer which serves as a conductive medium between electrodes and the gel. This format is known as submerged gel electrophoresis and it is the simplest to operate. Submerged gel electrophoresis is widely used for analysis of nucleic acids and agarose gels are the mostly used matrix.

A new synthetic matrix has been introduced for analysis of proteins and nucleic acids by Kozulic et al (U.S. patent application Ser. No. 328,123, Analytical Biochemistry 163 (1987) 506–512 and Analytical Biochemistry 170 (1988) 478–484). The matrix is based on an acrylic monomer, N-acryloyl-tris(hydroxymethyl)aminomethane (NAT). The poly(NAT) gels were found to be more porous than polyacrylamide gels but less porous than agarose gels. The gels were particularly suitable for separation of DNA molecules in size range from about 50 to a few thousand base pairs. However, as described in Kozulic (PCT/EP 92/00368), which is incorporated herein by reference, it was noticed that resolution of DNA in the poly(NAT) gels run in the submerged gel electrophoresis mode was never as good as in the vertical format. Subsequently, it was surprisingly observed that separated DNA bands in the submerged gel were bent, that is declined from the vertical axis. Such bending is detrimental for resolution because on a gel record, made by a camera positioned above the gel, the separated bands appear broad and diffuse. The cause of this bending was related mostly to ionic compositions of the gel and electrophoresis buffer. The bending could be eliminated or greatly reduced by adjustment of the ionic composition of the gel, as disclosed in the above cited document. The adjustment needed to be done each time after a considerable change in total monomer concentration, electrophoresis buffer or gel dimensions. Since these three variables are often changed in a research laboratory to improve resolution over a certain size range, it is apparent that a great amount of work would be saved if there were gels giving good DNA resolution in the range of up to a few thousand base pairs without being hampered by bending of bands at different gel concentrations and dimensions.

Agarose gels comprising about 0.6 to 1 percent polymer are suitable for separation of DNA molecules in size range from a few thousand to a few tens of thousand base pairs. The size range can be extended to several million base pairs by pulsed field electrophoresis (Cantor et al. Ann. Rev. Biophys. Biophys. Chem. 17 (1988) 287–304). Smaller DNA molecules require higher agarose concentrations for good resolution, as generally known in prior art. However, more concentrated agarose gels are difficult to prepare due to a high viscosity of agarose solutions. Furthermore, visualization of separated bands is difficult due to gel opacity. Derivatization of hydroxyl groups of agarose, as disclosed in U.S. Pat. No. 3,956,273 to Guisely, reduces viscosity of agarose solutions as well as gel opacity. Such hydroxyethylated agarose derivatives are commercially available products known under the trade name SeaPlaque and NuSieve (FMC Corporation). NuSieve agarose is typically used at polymer concentrations from about 2 to 8% and improved resolution of small DNA in this agarose has been reported (Dumais and Nochumson, BioTechniques, 5 (1987) 62). However, separated DNA bands were bent, although to a lesser degree than in poly(NAT) gels, also in NuSieve agarose gels containing as little as 4% of polymer (Kozulic, PCT/EP 92/00368). The bending could be reduced by adjustment of ionic composition of the gel, but as noted above it would be preferable to have a gel which does not require the adjustment.

The bending effect described was influenced by several factors but it was related mostly to difference in conductivity between the electrophoresis buffer and the gel immersed in that buffer. This difference in conductivity is caused by resistance of gel polymers to migration of buffer ions. The resistance, and therefore the difference in conductivity, may be presumably reduced by lowering the polymer concentration of the gel. However, there are many reports in prior art showing that lowering of polymer concentration compromises resolution of smaller biomolecules. For example, optimal resolution of small DNA molecules requires an increase of derivatized agarose concentration to up to 8–9% polymer dry weight (Dumais and Nochumson, BioTechniques, 5 (1987) 62). It should also be noted that improved resolution of proteins is achievable by first partially depolymerizing agarose and then preparing a gel having the polymer content of around 5–6% (Nochumson et al, PCT/US90/00184).

The belief that a gel of high polymer concentration is necessary for resolution of small biomolecules is supported by a theory based on the extended Ogston model of gel electrophoresis. This model considers a gel as a random network of fibers and states that the electrophoretic mobility of a macromolecule is proportional to the volume fraction of the pores of the gel that the macromolecule can enter (Rodbard and Chrambach, Proc. Natl. Acad. Sci. USA'65 (1970) 907–977 and Tietz, Adv. Electrophoresis 2 (1988) 109–169). The model also postulates that there is no contact between migrating molecules and gel fibers. The measured electrophoretic mobility, $\mu$, can be related to the free mobility in solution, $\mu_o$, of a migrating molecule with radius R, as well as to the gel percentage T, total length of the gel fibers, $1'$, and the fiber radius, r:

$$\log \mu = \log \mu_o - \pi 1'(r+R)^2 T \times 10^{-16} \tag{1}$$

or $$\log \mu = \log \mu_o - K_r T \quad (2)$$

where the retardation coefficient, $K_r$, is defined as $$K_r = \pi l'(r+R)^2 \times 10^{-16} \quad (3)$$

Separation of two DNA fragments a and b can be written as $\Delta\mu = \mu_a - \mu_b = \mu_{oa} e^{-K_{ra}T} - \mu_{ob} e^{-K_{rb}T}$. Since the free mobility $\mu_o$ of all DNA molecules is equal (Olivera et al., Biopolymers 2, (1964) 245–257) and maximal separation occurs when $d(\Delta\mu)/dT=0$, gel concentration T giving optimal resolution is:

$$T = \ln(K_{ra}/K_{rb})/(K_{ra}-K_{rb}) \quad (4)$$

This equation corresponds to equation 25 of Rodbard and Chrambach (Proc. Natl. Acad. Sci. 65 (1970) 970–977). From that equation it follows that as Kra decreases, that is size of DNA fragment a becomes smaller, the gel concentration T necessary for resolution of fragments a and b increases. As noted above, however, when a gel of high polymer concentration is run in the submerged electrophoresis mode, separated bands are bent. Accordingly, from the prior art it seemed impossible to achieve optimal resolution by submerged gel electrophoresis without necessary adjustment of gel ionic composition in order to control the bending of separated bands.

The extended Ogston model teaches that very small ions are also retarded in a gel because even when radius R of an ion is zero, retardation coefficient is higher than zero (equation 1). However, from that equation it is not possible to predict at which minimal gel concentration, if any, resistance to migration of buffer ions is so small that the difference in gel and buffer conductivity does not significantly affect the bending of bands. Experiments were designed in an attempt to find out whether there is such a gel comprising synthetic polymers, since resolution of macromolecules of small size in low percentage agarose gels is known to be inferior. In practice, the lowest workable concentration of a synthetic gel is determined by its mechanical stability which in turn depends mostly on polymerization efficiency of a starting monomer solution of a low concentration. This is true for acrylamide as well as many other hydrophilic and amphiphatic gels disclosed in (Kozulic and Heimgartner, U.S. patent applications Ser. Nos. 293,840 and 696,696), which are incorporated herein by reference. The lowest practical gel concentration is in most cases around 4%. Since in 4% gels bending of bands was still noticeable (Kozulic, PCT/EP 92/00368), it appeared important to find a way for preparation of gels of even lower percentage. Most gels in prior art were polymerized in presence of a cross-linker having two vinyl double bonds but in some of them the cross-linker was a polymer with plurality of double bonds. That cross-linker was an agarose polymer substituted with allyl glycidyl ether (U.S. Pat. No. 4,504,641 to Nochumson), which is known as Acryl Aide® (FMC Corporation). Since a mechanically more stable, low percentage gel was desirable, in an attempt to obtain such a gel the Acryl Aide® agarose polymer was cross-linked through its hydroxyl groups prior to copolymerization. It was reasoned that a single large and branched cross-linked vinyl-agarose polymer will cross-link during polymerization many chains formed from the polymerizing monomer and thus improve mechanical stability of the matrix and resolution of small biomolecules. In an initial experiment, 6% poly(NAT) gels were polymerized with different amounts of the cross-linked vinyl-agarose. Transparency and mechanical strength of the resulting gels looked standard. During electrophoresis migration rate of the bromphenol blue tracking dye was normal. However, totally unexpectedly it was observed that resolution of DNA molecules was progressively lost as the amount of the cross-linked vinyl-agarose increased and at a certain cross-linker concentration there was no resolution at all. Surprisingly, the resolution was lost even when DNA fragments migrated essentially the same distance as in the control gel. At higher cross-linker concentrations the loss of resolution was accompanied by reduced migration rates. The loss of resolution occurred first in the low molecular weight range.

The above experimental data appeared to be of limited practical importance but they were a clue that lead to development of a new model for electrophoretic migration of macromolecules in gels. The model is described herein as follows. A gel is regarded as a block comprising randomly distributed polymer chains and water. The polymer chains have different motional freedom along their length. Regions of high motional freedom are separated by spots of low motional freedom, which correspond to cross-linking points in synthetic gels. There are no pores of any finite shape or size in transparent gels. Accordingly, there is no defined space or volume a macromolecule can enter before it begins to migrate in electric field. Once it starts migrating, the macromolecule pushes the polymer chains and thus creates the space it occupies. The macromolecules move along their path in discrete steps and in each step they pass through one gel layer. The gel layer is defined as a gel cross-section perpendicular to direction of migrating molecules. A gel layer is thicker than radius of the polymer chain but thinner than radius or length of the migrating macromolecule. Thus, the migrating molecule may encounter a second layer before it completely passes through the first one, however, resistance to its migration is given only by the second layer. Essential to this model is the notion that there are two ways a macromolecule can pass trough a layer. Thus, it will push aside polymer chains when on its path the macromolecule encounters a region in which polymers have a high motional freedom. In this way the macromolecule will open a "door" in the layer. When on its path the macromolecule encounters an area where polymers have a low motional freedom, it deforms the layer until an opening is formed. This opening is created at places where one or more polymer chains end or where the polymer chains are less cross-linked or entangled. The macromolecule thus creates a "corridor" in the layer. Creation of a "corridor" in one layer is accompanied by dislocation of some polymer chains in at least one layer above and below. If the migrating macromolecule encounters a similar place on the next layer, it will again open a "corridor". These two "corridors" may be connected into a single one and thus the same "corridor" can span several layers.

Whether a macromolecule will predominantly open "doors" or "corridors" on its way through the layers depends entirely on the balance of two forces. The first force acting on the layer is electrokinetic and it is exercised by all macroions moving in an electric field. This force is countered by resistance of polymer chains comprising the layer. The polymer chains resist to any change in their arrangement because during gel formation they have acquired energetically the most favorable position. When magnitude of the electrokinetic force in relation to resistance of polymer chains is high, "corridors" will be predominantly formed. When the two forces are of similar magnitude, a part of the openings will be "doors" and part "corridors". When the ratio of electrokinetic force and resistance is small, then the openings in layers will be predominantly "doors".

On a time scale, formation of "doors" is faster than formation of "corridors" because the migrating molecules can faster form openings by pushing aside one or a few polymer chains than by deforming a part of gel layer consisting of many polymer chains. In case of DNA fragments, which have a constant charge to size ratio, longer fragments exercise stronger forces but they migrate slower because the openings they create are mostly "corridors". It is postulated that resolution of macromolecules is good when on their way through layers they open both "doors" and "corridors". There is little or no resolution when they open only "doors" or only "corridors", however, gel structure must be such that macromolecules are able to open "corridors". Accordingly, polymers of different layers must be connected in such a way that they can be dislocated sufficiently to open the "corridors". The "corridors" cannot be opened and there is no resolution when polymer chains of different layers are connected with a large, branched cross-linker, such as the one described above.

The new model predicts that if some molecules were to open "corridors" in most layers, they would migrate faster than those which open both "doors" and "corridors" since, as one "corridor" can span several layers, such molecules would pass through these layers in one step. In other words, in some gels larger molecules may migrate faster than smaller ones even at a low electric field strength. An example supporting the above prediction is presented herein. Thus, it was found that in an unidirectional electric field at 7 V/cm a 23 kbp DNA fragment migrated faster than a 9.4 kbp fragment in a standard 6% poly(NAT) gel cross-linked with Bis. This result cannot be explained in terms of the extended Ogston model because, according to equation 1, larger molecules always have a higher retardation coefficient and therefore migrate slower. Furthermore, the above result is not in accordance with the reptation model of DNA gel electrophoresis (Lumpkin et al, Biopolymers 24 (1985) 1573–1593), which states that resolution of DNA molecules above certain size is lost because all of them migrate with the same velocity in a homogenous electric field. Many experimental findings reported in prior art that have been difficult or impossible to explain can be accounted for by the model presented here but that is out of current scope.

In prior art faster or slower electrophoretic migration has been generally related to higher or lower gel porosity. Although the model presented herein states that in transparent gels macromolecules do not move through pores, because the pores do not exist, the terms "porosity" and "effective porosity" will be used hereinunder for the sake of easier comparison with results reported in prior art. One additional reason is that in many reports in prior art there is no reference to transparency of the gels used.

The above model was based on experimental data obtained with gels comprising synthetic polymers. In order to better corroborate the new model, it was desirable to obtain supporting results with gels comprising natural polymers. Since the cross-linked vinyl-agarose polymer was used as a gel component in the above mentioned crucial experiment, it appeared reasonable to assume that cross-linked agarose gels will exhibit a similar behavior, that is deteriorating resolution after cross-linking. It is widely known that agarose polymers dissolve at a high temperature and by cooling form gels suitable for electrophoresis. If the cross-linking reaction were carried out at a temperature where agarose polymers are still fully in solution, it was reasoned that they would cross-link in such a way that "corridors" could not open in the resulting gel, if a gel formed. To verify this hypothesis, into a 1% agarose solution epichlorhydrin and sodium hydroxide were added and the mixture incubated at 45° and 65° C. It was observed that control agarose solutions without the cross-linker did not solidify into a manageable gel at either of the two temperatures, but in the presence of epichlorhydrin a gel was formed at both temperatures. Surprisingly, both gels were fully transparent, in contrast to the characteristic opacity of standard 1% agarose gels. Electrophoresis of DNA fragments resulted in poor resolution in the gel cross-linked at 65° C., especially in the 200–600 bp range. Unexpectedly, however, electrophoresis under the same conditions in the gel cross-linked at 45° C. gave very good resolution of DNA fragments, also in the 200–600 bp range. Now that this surprising result was known, it was sensible to test other cross-linkers and cross-linking conditions. The general features of the above experiment remained constant, that is gel formation and cross-linking reaction proceeded simultaneously in a water solution of dissolved agarose. The gel was always in form of a continuous bed. Further, the cross-linkers reacted with hydroxyl groups of polymers to form ether linkages without introducing a charged group into the gel.

Several different cross-linked agarose derivatives are known in prior art. Thus, U.S. Pat. No. 3,507,851 to Ghetie discloses cross-linking of agarose particles with epichlorhydrin. U.S. Pat. No. 3,959,251 and UK Patent 1,352,613 both to Porath et al. disclose stabilization of agarose beads by cross-linking with several bifunctional reagents in the presence of a reducing agent. The resulting beads were more rigid, giving higher flow rates when packed into columns for chromatography. The processes and products of Ghetie and Porath are clearly different from those presented here. Thus, the cross-linking reaction was carried out after the gel was formed and the resulting products were in form of particles.

Cross-linked agarose gels in form of plates are also known. Thus, U.S. Pat. No. 3,860,573 to Honkanen discloses agarose gels cross-linked with a bifunctional reagent containing two equal functional groups selected from acyl chloride, sulfonyl chloride and isothiocyanate. The cross-linking reaction was carried out in an organic solvent with suspended and not dissolved agarose polymer. The reaction could not have been performed successfully in water because compounds having the said functional groups react fast with water. The bonds formed with bifunctional reagents were esters, sulfonates or thiocarbamates. Moreover, as some cross-linker molecules must have reacted through only one functional group, the other functional group hydrolyzed when the gel was brought into contact with water. This side reaction introduced charged groups, such as carboxylic and sulfonic, into the matrix. Due to above mentioned differences, the process and products of Honkanen are profoundly different from those disclosed herein.

Another process for treatment of polysaccharide gels comprises suspending or dissolving the polysaccharide gel in a solution of 2,4,6-trichloro-1,3,5-triazine, as disclosed in U.S. Pat. No. 3,956,272 to Tixier. The resulting strengthened gel may be in form of plates. Regarding the process of Tixier, it should be noted that the triazine ring of the starting cross-linker is incorporated into the agarose matrix. Moreover, each of the three cross-linker chlorine atoms had the possibility to react with either hydroxyl groups of agarose or water. Therefore some of the incorporated triazine molecules were inevitable converted to cyanuric acid derivatives, that is to compounds containing one or two hydroxyl groups at carbon atoms initially linked to chlorine. These hydroxyl groups are known to have a low pK value, and as such are charged at a high pH. In addition, each triazine ring contains three nitrogen atoms and, as a tertiary amine, triazine will be protonated at a low pH. Therefore, the cross-linking reaction of Tixier introduces into the gel a chemical group which is charged.

Honkanen and Tixier reported that their cross-linked agarose gels could be used as media for electrophoresis. Regarding properties of these matrices, Honkanen teaches that movement of large molecules (proteins) is more rapid in the cross-linked agarose, which would indicate an increase of effective porosity due to the cross-linking reaction. Tixier discloses that the treated gels had essentially the same characteristics as untreated gels with respect to sieving and resolving power. This result of Tixier is in accordance with the report of Porath (J. Chromatogr. 103 (1975) 49–62) who found that cross-linked agarose beads did not change their porosity. Accordingly, the reduced migration of large protein molecules and medium size DNA as well as dramatically improved resolution observed in the cross-linked gels disclosed herein are totally unexpected. Moreover, profound improvement in transparency of the gels of present invention is surprising, because neither Honkanen nor Tixier mention that opacity of their gels changed with the cross-linking.

In the prior art known are also electrophoresis gels comprising derivatized agarose. Thus, U.S. Pat. Nos. 3,956,273 to Guisely and 4,319,975 to Cook disclose many derivatized agarose polymers. After a derivatization reaction the polymers were purified and dried. To form a gel for electrophoresis, the dried polymer particles were dissolved in hot water and the solution cooled. Although majority of the modifying reagents were monofunctional, a bifunctional reagent could also be employed. However, Guisely teaches that the ratio of the bifunctional reagent to agarose as well as derivatization conditions must be such that the polymer chains are not cross-linked, since otherwise the resulting product could not be redissolved as required for subsequent preparation of the electrophoresis gel. Accordingly, even though Guisely and the present process use one common cross-linker, epichlorhydrin, the processes are different because in the present process the cross-linker reaction and formation of gel for electrophoresis occur simultaneously and the ratio of the cross-linker to agarose is much higher. These differences in processes resulted in different products, so that products of the present invention are, among other characteristics, water insoluble whereas the agarose gels of Guisely and Cook can be redissolved by heating.

Other ways of changing some properties of agarose gels are also known in prior art. For example, electroendosmosis can be eliminated by mixing agarose with another polysaccharide (U.S. Pat. No. 4,290,911), resolution of LDH isoenzymes can be improved by addition of an acidic polysaccharide (U.S. Pat. No. 4,321,121) and gel porosity can be continuously varied by using a salt gradient during gelation (U.S. Pat. No. 5,009,759).

The gels discussed above comprised agarose polymers. These polymers are composed of D-galactose and 3,6-anhydro-L-galactose, linked in alpha 1–4 linkages and thus forming linear polymers. Branched polysaccharide polymers are also widely known, and some of them have been employed in preparation of gels for electrophoresis. Thus, gels made of starch are one of the oldest media for electrophoresis. As disclosed in U.S. Pat. No. 4,094,832 to Soderberg, derivatized dextran polymers may also serve as a component of gels for electrophoresis. The dextran polymers were chemically modified in such a way that hydroxyl groups in glucose units were substituted for functional groups containing double bonds. Gel formation occurred by free radical polymerization when these double bonds polymerized or copolymerized with a small molecular weight monomer. Soderberg mentioned the possibility to cross-link dextran chains with a small cross-linker in order to make a gel for electrophoresis, however, this possibility was deemed unpractical because removal of the cross-linking reaction byproducts by diffusion would require months to complete. Whereas this is true for vertical slab or tube gels, removal of the byproducts is fast in gels for submerged gel electrophoresis because the top side of these gels is open and thus diffusion path is short. From Soderberg it is possible to infer that, if a practical way for removal of byproducts were found, gels composed of cross-linked dextran would be suitable for electrophoresis. However, as disclosed hereinunder, gels composed of this branched polysaccharide were found unsuitable.

OBJECTIVES OF THE INVENTION

It is an objective of the current invention to provide electrophoresis gels giving improved resolution of small biomolecules.

It is another objective of the present invention to provide electrophoresis gels of such a low polymer concentration that separated bands in the gel are not bent.

It is a further objective of the present invention to provide electrophoresis gels with improved optical properties.

A further objective of the present invention is the provision of novel method using as the electrophoresis medium a gel of the present invention.

Other features and advantages of the present invention will become more apparent from an examination of the following specification when read in conjunction with the appended drawings, in which:

DETAILED DESCRIPTION OF THE INVENTION

Figure 1:
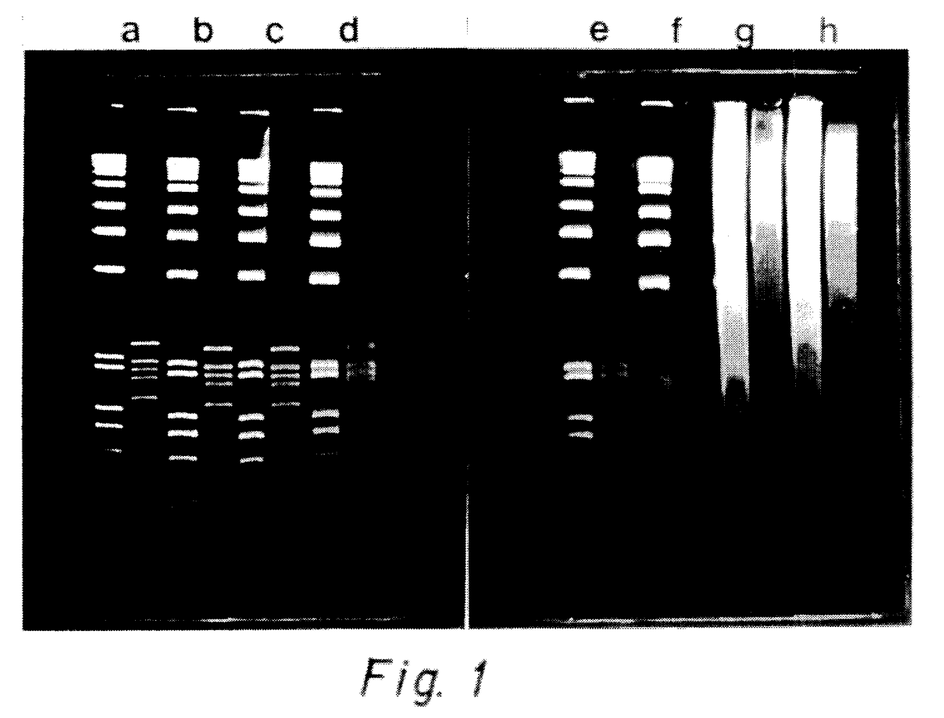
FIG. 1 shows eight different poly(NAT) gels (a-h) of the same monomer and cross-linker concentration (T=6 and C=3%) but differing in the ratio of the linear and branched polymeric cross-linker, as described in Example 1. The ratio of the branched cross-linker increases from a to h.

Bands representing separated species are bent in a submerged electrophoresis gel containing a high polymer concentration and the same buffer as a running buffer. The bending effect is related mostly to a difference in current density/specific conductivity ratio between the electrophoresis buffer and the gel immersed in that buffer (Kozulic, PCT/EP 92/00368). This difference exists because of resistance of polymer chains to migration of buffer ions and due possibly to a change of relative migration rates of ions in the gel and buffer. The resistance, and therefore the difference in conductivity, may be reduced by lowering the polymer concentration of a gel. In an attempt to find out whether there is a synthetic gel of a suitably low polymer concentration, a new macromolecular, branched cross-linker was prepared assuming that this cross-linker will improve stability and resolution of the gel by cross-linking during polymerization many chains formed from the polymerizing monomer. The preparation of this cross-linker as well as gels cross-linked with it is described in Example 1. FIG. 1 shows separation of DNA restriction fragments in gels containing increasing concentration of the branched cross-linker. In addition to the branched cross-linker, each gel contained the linear polymeric cross-linker from which the branched one was prepared. The weight sum of the two cross-linkers was constant in all gels. As can be seen from FIG. 1, already a small quantity of the branched cross-linker impairs resolution in the low molecular weight range and the loss of resolution is more pronounced at higher ratios of the branched cross-linker. There is also a gradual worsening of resolution among larger fragments and the resolution is completely lost at a certain amount of the branched cross-linker. The gels cross-linked with the branched cross-linker were essentially as transparent as the gel containing only the linear cross-linker.

The result shown in FIG. 1 can be explained by the new model of gel electrophoresis which states that macromolecules deform gel layers as they migrate. The branched cross-linker interfered with the deformation of gel layers and therefore the resolution was lost. An additional result supporting the new model is presented in FIG. 2. It shows two-dimensional electrophoresis of DNA fragments varying in size from 2.0 to 23 kbp in a 6% poly(NAT) gel. In the first dimension the DNA molecules were run at 2 V/cm for 32 h and then the gel was turned by 90° and electrophoresis continued for 5 h at 7 V/cm. At 2 V/cm the migration order of the DNA fragments was as expected, that is the largest fragment migrated the shortest distance. However, at 7 V/cm the largest fragment (23 kbp) migrated faster than the second largest fragment (9.4 kbp). This experimental result cannot be explained by the extended Ogston model nor reptation model of gel electrophoresis.

The branched cross-linker used in Example 1 was a derivative of agarose. In an attempt to further confirm the new model of gel electrophoresis, underivatized agarose polymers were cross-linked with the same cross-linker, epichlorhydrin, employed for preparation of the branched vinyl cross-linker. The cross-linker to agarose ratio was essentially equal to that used to cross-link the vinyl-agarose polymer. The cross-linking reaction was carried out at different temperatures because agarose polymers are at equilibrium with the gel form over a broad temperature range (FMC Source Book). Thus, after addition of sodium hydroxide and epichlorhydrin to a 1% agarose solution, the mixture was incubated at 45° and 65° C. As a control, an agarose solution without epichlorhydrin but with sodium hydroxide was incubated at the same temperatures. After overnight incubation, it was observed that the control agarose solutions did not solidify into a manageable gel at either of the two temperatures, but in the presence of epichlorhydrin a gel was formed at both temperatures. In contrast to characteristic opacity of standard 1% agarose gels, the cross-linked gels were fully transparent. After electrophoresis of DNA fragments, resolution in the gel cross-linked at 65° C. (FIG. 3) was poor, especially in the 200–600 bp range. Unexpectedly, electrophoresis under the same conditions in the gel cross-linked at 45° C. gave very good resolution of DNA fragments, also in the 200–600 bp range (FIG. 4). Knowing this surprising result, it was reasonable to test other cross-linkers and cross-linking conditions to find out whether the gel shown in FIG. 4 is exceptional or whether there are other cross-linkers, polymers and cross-linking conditions giving gels of similar suitability for high resolution electrophoresis. The general features of the initial cross-linking experiment remained constant, that is gel formation and cross-linking reaction proceeded simultaneously in a water solution of dissolved polymer. The gel was always in form of a continuous bed. Further, the cross-linkers reacted with hydroxyl groups of polymers to form ether linkages without introducing a charged group into the gel.

There are many hydroxyl groups containing polymers and many cross-linkers able to react with these hydroxyl groups to form ether linkages. The polymers may be of synthetic or natural origin and illustrative examples of the polymers include polyvinyl alcohol, hydroxyethyl methacrylate, hydroxyethyl cellulose, agar, agarose, gellan, pullulan, starch and dextran. In one embodiment more than one linear polysaccharide may be used such as agarose and hydroxyethyl cellose. A gel comprising agarose, hydroxyethyl cellulose and dextran or starch may also be produced. Some polymers, like hydroxyethyl cellulose, remain as viscous water solutions whereas the others, like agarose, form thermally reversible gels. The suitable cross-linkers may have functional groups of equal or different reactivities and illustrative examples comprise bis-epoxides, halo-epoxides, bis-haloalkanes, bis-haloalcohols, alkanediol bis-alkyl or aryl sulfonates and divinylsulfone. The reactive groups of the cross-linkers may be of different type, however, ether bonds must be formed from both groups after reaction with hydroxyl groups from the polymer. Other polymers and cross-linkers not mentioned here will suggest themselves to those skilled in the art.

Gels of the present invention are formed by reacting a hydroxyl group containing polymer with a cross-linker able to link the polymer chains through ether linkages. The properties of so formed gels depend not only on the particular polymer and cross-linker but also on the cross-linking conditions. This fact has already been demonstrated (FIGS. 3–4) and will be further documented hereinunder. There are several important factors which need to be considered when choosing the cross-linking conditions. Thus, the polymer must be stable during the reaction, that is other functional groups, if present, should not be unspecifically affected. For example, bisepoxides react with hydroxyl groups under both acidic and basic conditions but when the polymer is a polysaccharide, then the cross-linking reaction should be performed at a basic pH because glycosidic bonds in polysaccharides are not stable at a low pH. Moreover, the cross-linking reaction should be carried out in the absence of any compound which would introduce a charged group into the gel after reacting with a functional group of the cross-linker. In particular, amines should be avoided. An exception to this rule may exist if the starting polymer is slightly charged and a small number of opposite charges needs to be introduced into the gel in order to balance positive and negative charges of the matrix, for reasons disclosed in U.S. Pat. No. 4,312,739. Compounds having hydroxyl groups or compounds with no reactive group may be present, if desirable, during the cross-linking reaction.

Since according to teaching of the present invention the cross-linking reaction is performed in water, hydrolysis of the reactive groups present in the cross-linker is an unavoidable side reaction. This side reaction deserves a detailed consideration. Taking epichlorhydrin as a model cross-linker, reaction with one water molecule gives glycidol or 3-chloro-1,2-propanediol, depending whether chloride is substituted or epoxide opened. In both cases the reaction with one additional water molecule will give glycerol. Glycidol and 3-chloro-1,2-propanediol can also react with polymer hydroxyl groups. After such a reaction there will be no cross-linking of the polymer chains, instead the polymer will be substituted with a glycerol (propane-2,3-diol) moiety. This glycerol moiety on the polymer can react with epichlorhydrin and thus participate in the cross-linking of polymer chains. Alternatively, the polymer glycerol moiety may react with another glycidol or 3-chloro-1,2-propanediol molecule, thus extending the length of the substituent. Moreover, glycidol or 3-chloro-1,2-propanediol can react with an epichlorhydrin molecule and thus form a new cross-linker. Functional groups in this new cross-linker will be at a larger distance and therefore the new cross-linker is able to react with two hydroxyl groups on the polymer that are too distant to be cross-linked by a single epichlorhydrin molecule. Moreover, the glycerol formed can react with three epichlorhydrin molecules forming a novel cross-linker with three functional groups. Analogous reactions leading to formation of other polyfunctional cross-linkers are easy to formulate. The formation of such compounds has already been suggested and it has been indicated that polymer hydroxyl groups react predominantly through these secondary cross-linkers derived from epichlorhydrin (EP 0 203 049 B1).

There are several important consequences of the above reactions. Thus, the length of the cross-links, be it intermolecular or intramolecular, is not constant but varies significantly. Furthermore, it is evident that even when the starting cross-linker is bifunctional it does not mean that only two polymer hydroxyl groups participate in all cross-links. A single newly formed polyfunctional cross-linker may cross-link not only two but three or more hydroxyl groups and thus more than two polymer chains. In prior art known are also trifunctioanal and tetrafunctional cross-linkers (EP 0 132 244 B1), and if desirable they can also be used as the starting cross-linkers.

From the above considerations it is clear that the gel structure includes units derived from the polymer and cross-linker. The units derived from the cross-linker are heterogenous, that is they differ in size and structure. These units can be long or short and branched or linear. Gel properties will depend not only on the number of cross-linking points but also on the size and structure of the cross-links. On the polymer chains there will exist inevitably also substituents which are not cross-links. The relative proportions of the cross-links and substituents as well as their size and structure depend on several variables including the initial polymer/cross-linker ratio, type of the cross-linker as well as temperature, pH and reaction time. Due to complexity of the cross-linking reaction and accompanying gel formation it is difficult to predict the exact experimental conditions giving a gel of desirable properties. Such a gel can be obtained only by systematic variation of the reaction parameters.

In practice of the present invention, there are several important parameters which exert a profound influence on properties of the gels. Thus, the choice of the starting polymer is of major importance. It is possible to use a synthetic or natural polymer possessing hydroxyl groups. Synthetic polymers are usually more chemically stable and more resistant to microbial attack, which may be essential for long term storage of the gels. On the other hand, synthetic polymers tend to be more hydrophobic than the natural ones and therefore, when the electrophoretic separation of biomolecules is to be based exclusively on their charge and size, natural polymers are preferable. The polymer choice depends also on its water solubility and size. It is advantageous to dissolve the polymer to at least 1% (w/v), preferable up to about 10%. The molecular mass of the polymer should not be lower than about 10,000 Da but it may be as high as several million Daltons, preferable it should be in the range of 50,000 to 500,000 Da. A water solution of the polymer may be such that a gel would form by changing pH or temperature. Alternatively, the polymer may remain as a water solution over the whole temperature (0°–100° C.) and pH (0–14) range. When desirable, more than one of the above polymers may be used so that a single gel will comprise units derived from different polymers.

The choice of a reagent that will cross-link the polymer chains is very important. The cross-linker must possess chemical groups which readily react with hydroxyl groups from the polymers in a water solution under conditions which are compatible with stability of the polymer. The cross-linker itself must be uncharged and must not give rise to a side reaction giving a charged compound which can be incorporated into the matrix. The cross-linker should also be hydrophilic. Reaction of water with its reactive groups should result in formation of an alcohol. The reactive groups in the cross-linker molecule may be chemically equivalent or they may be of different chemical reactivity. The reaction between hydroxyl groups from the polymer and reactive groups of the cross-linker may be of different type, such as addition, substitution or ring opening. The reaction may be catalyzed by acids or bases and one or more base equivalents may be consumed during the reaction. In some cases a salt may be produced as a byproduct. It is of course possible to use a mixture of at least two cross-linkers so that the matrix will comprise units derived from more than one cross-linker. The cross-linker may be diluted with a solvent prior to its addition into a water solution of the polymer.

As noted above, both synthetic and natural polymers can be used in practice of the present invention. Natural polymers are preferred because of their pronounced hydrophilicity. There are many hydrophilic polymers of natural origin but suitable for electrophoretic applications are only those which are essentially charge free or those which possess only a small number of charges. Most common of such polymers are agarose, derivatized cellulose, starch and dextran. Of many chemical compounds which satisfy the requirements for a possible cross-linker, preferred are relatively small molecules with molecular weight less than 500. Compounds having oxirane groups are particularly suitable as well as those possessing oxirane and halo groups. Other suitable cross-linkers are those with two or more halo groups or with good leaving groups other than a halogen. Compounds whose reactive double bonds react with hydroxyl groups are also suitable. Examples of the cross-linkers with an oxirane group include epichlorhydrin, butanediol diglycidylether and ethyleneglycol diglycidylether. The cross-linkers with halo groups comprise 1,2-dibromo-propanol and 1,3-dichloropropanol whereas divinyl sulfone is an example of a suitable cross-linker with activated double bonds.

Due to better stability of the preferred polysaccharide polymers at higher pH values, the cross-linking reaction was carried out under basic conditions. Different bases can be used but preferred are inorganic hydroxides and most preferred are sodium and potassium hydroxide. Depending on the cross-linker type, a base may act as the reaction catalyst or it can be also consumed in the reaction. Thus, there is no base consumption when using divinyl sulfone or butanediol diglycidylether but one mole of base is consumed for every epichlorhydrin molecule. Two base equivalents are necessary for the cross-linking reactions with, for example, 1,3-dichloropropanol. Base consumption during the cross-linking reaction requires addition of a considerable amount of an alkali hydroxide at the beginning of the reaction. Periodic additions are not possible because gel formation would be disturbed. This means that, at least initially, the reaction conditions are more harsh when such cross-linkers are used. In addition, a salt is formed as a byproduct. The presence of a salt during gelation may influence gel structure in some cases, as it was demonstrated for agarose gels (U.S. Pat. No. 5,009,759). Furthermore, since prior to an electrophoretic separation salts need to be removed, gel equilibration requires more time and/or longer washes when there is a high salt concentration inside the gel.

Gel properties depend also on the polymer concentration. The choice of polymer concentration relies on its water solubility and desirable gel properties, such as mechanical stability and separation range. Good mechanical stability and optimal separation were achieved at different polymer concentrations when the gels comprised different starting polymers. For example, the preferred polysaccharide polymer concentration with standard commercial agarose preparations was from about 0.5 to 2%. The concentration of hydroxyethyl cellulose polymers giving handleable polymer solutions and suitable gels was from about 3 to about 6%. Dextran polymers formed gels of good mechanical stability when the polymer concentration was from about 5 to about 10%. Separation of biomolecules in the above gels was dependent on both the polymer type and concentration. Thus, the quality of separation was much better in agarose and hydroxyethyl cellulose than in dextran gels. Moreover, dextran gels had a strong tendency to swell so that the sample wells deformed, which further confounded sharpness of the separated bands. Attempted cross-linking of another branched polysaccharide, starch, did not result in a manageable gel under the experimental conditions tested. Accordingly, even though the starting polymers were all polysaccharides, their cross-linking resulted in different gels, if gels formed. The superiority of gels comprising linear polysaccharides for electrophoretic applications is in accordance with the model of gel electrophoresis presented herein.

Cross-linker type and concentration also determine gel characteristics. The suitable cross-linker concentrations were dependent strongly on the cross-linker type, which is not surprising given the greatly different reactivities of the chemical groups of the cross-linkers. Thus, dimyl sulfone produced gels at the lowest concentration of all tested cross-linkers (0.1–0.5%, v/v) whereas the concentration of other cross-linkers was typically above 1%, v/v. The reactive groups of the cross-linkers were usually in a molar excess over hydroxyl groups in the polymer. The need for an excess of the cross-linkers indicates that reactions with water are faster than with polymer hydroxyl groups. Divinyl sulfone seems to have the best selectivity for polymer hydroxyl groups but its high toxicity is a concern.

The cross-linking reaction proceeded for different time periods. The reaction time and temperature of any chemical reaction are known to be interconnected, because in general reaction rates increase with temperature. For preparation of gels according to teaching of the present invention, the reaction time was varied from about 15 minutes to 5 days. The shortest time periods were possible with divinyl sulfone which, under certain conditions, reacted so -fast that a gel formed before the reaction solution could be poured into a mold. On the other hand, bis-oxirane cross-linkers reacted much slower so that no changes in the electrophoretic pattern of DNA fragments could be demonstrated only after a several day long incubation.

Byproducts are formed during gel formation. They include nonionic and ionic species. Ionic species result from a cross-linker having a leaving group. The formed gels contain also the base which is used as a catalyst and/or reactant. The gels may also contain some unreacted cross-linker if the reaction conditions were not optimal. For electrophoretic applications it is important that ionic composition of a gel is well defined. The simplest way to achieve this goal is to wash the gel in water followed by incubation in a desirable electrophoresis buffer. When the gel is intended for use in submerged gel electrophoresis mode then equilibration is easy because at least five gel sides are open so that diffusion paths are short. For easy handling, it was found very convenient to fix the gel during its formation to a plastic support, such as Gel Bond (FMC Corporation). Gels of the present invention can be cast also in a vertical mode between two plates. Such gels can be equilibrated electrophoretically, that is upon application of a voltage gradient, all ionic species would migrate out of the gel. There would still be nonionic byproducts left, however, provided that all reactive groups of the cross-linker have reacted, these byproduct can be only alcohols and their presence is compatible with electrophoresis of biomolecules.

Gels formed by reacting many different polymer/cross-linker combinations under various cross-linking conditions are described in the illustrative examples below. Properties of these gels, including electrophoretic separation of DNA and proteins, are reported in specific examples but some general conclusions can be made on basis of the reported results. Thus, for a particular polymer/cross-linker pair there is a polymer and cross-linker concentration which under defined conditions gives a gel with optimal properties regarding electrophoretic separation of biomolecules over a certain size range. When the same polymer is cross-linked with another cross-linker under identical conditions, a gel with different separation properties is formed. For example, DNA fragments migrated further in a gel comprising 1% agarose polymers cross-linked with epichlorhydrin than in a 1% gel cross-linked with butanediol diglycidylether (Examples 4 and 6). Gels comprising more than one polymer also gave good separations. Migration distances in these gels depended not only on the polymer concentration but also on the relative ratios of the polymers (Example 16). When a gelling polysaccharide, agarose, was used there were pronounced changes in several properties of the new gels compared to those of the standard gels obtained merely by temperature induced gelation. Thus, gels of the present invention could not be redissolved by heating. In addition, whereas gels obtained by cooling of agarose solutions were hard and brittle, the gels formed according to the present invention were soft and elastic. The improved elasticity of the present agarose gels is in contrast with the increased rigidity of the cross-linked agarose gels for chromatography, as described in J. Chromatogr. 103 (1975) 49–62 and U.S. Pat. No. 3,959,251. Moreover, some agarose gels prepared from solutions with a constant polymer concentration but increasing cross-linker concentration showed a gradual reduction in migration velocity of biomolecules only up to a certain cross-linker concentration. When the cross-linker concentration was raised above that value then, surprisingly, biomolecules migrated a longer distance than in gels with less cross-linker (Example 7).

Figure 5:
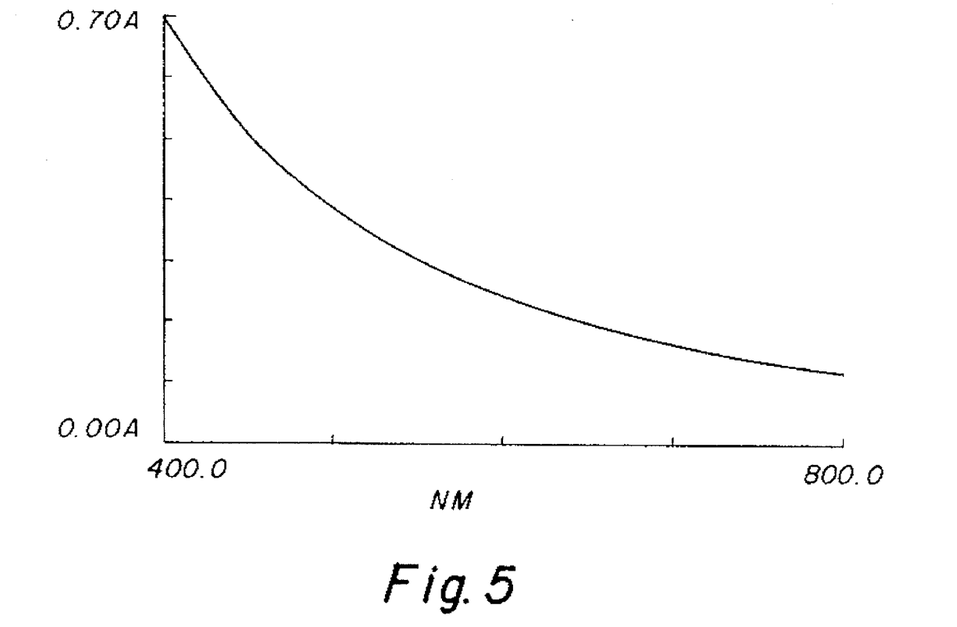
FIG. 5 is a visible spectrum of a standard 2% agarose gel.
Figure 6:
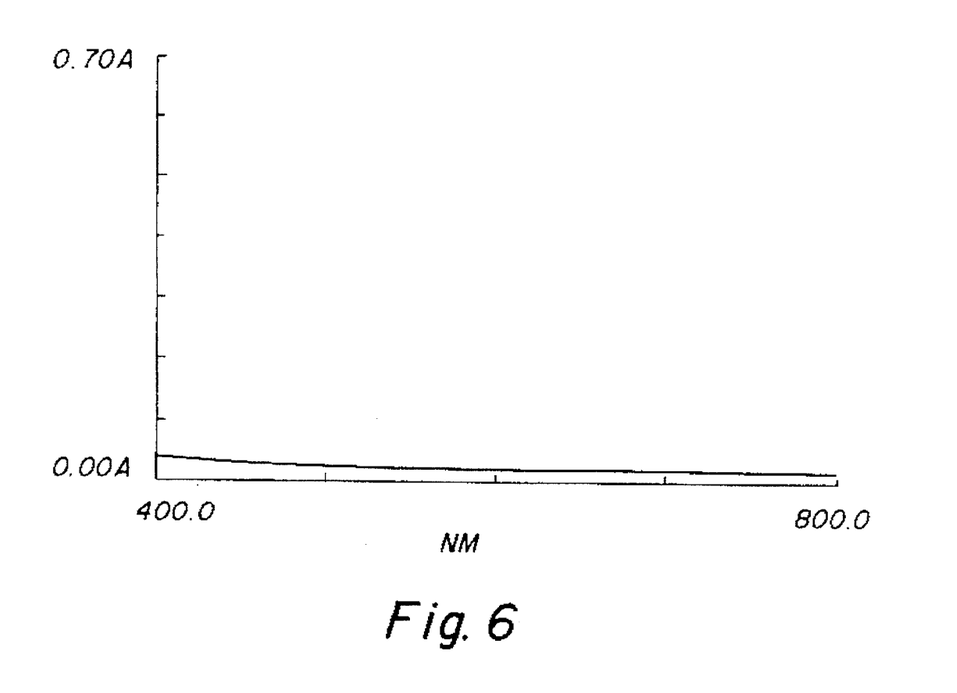
FIG. 6 is a visible spectrum of a gel comprising 2% of agarose polymers and 2 mmol of 1,3-dichloropropanol in 10 ml of gelling solution.
Figure 7:
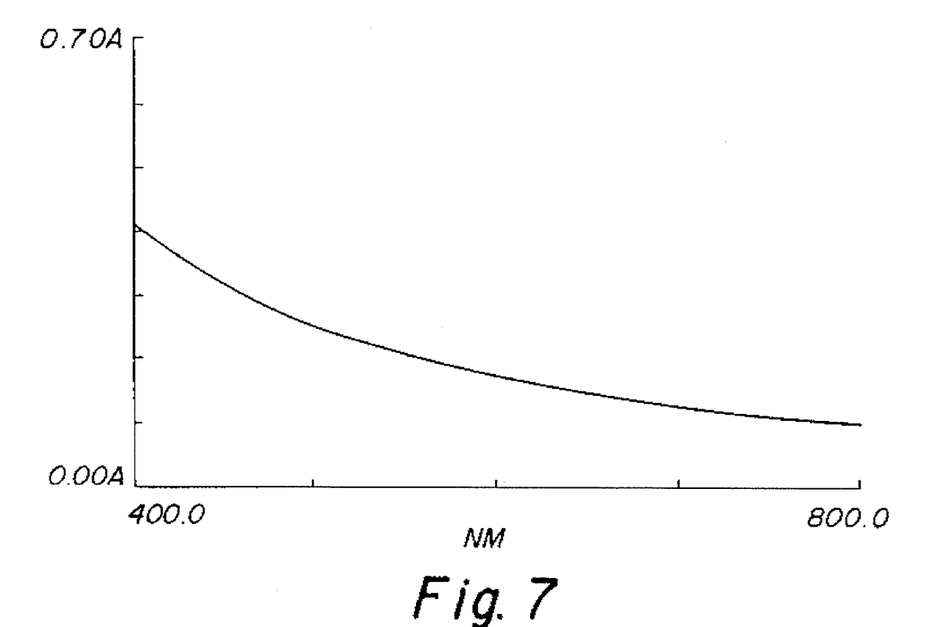
FIG. 7 is a visible spectrum of a 2% gel prepared from hydroxyethylated agarose (SeaPlaque).
Figure 8:
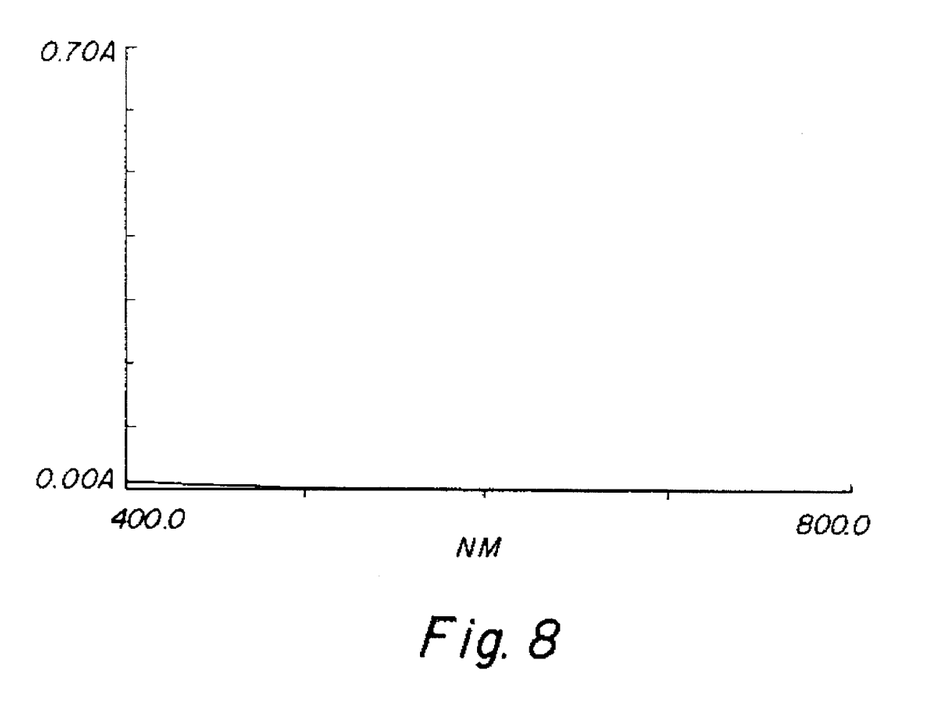
FIG. 8 a is visible spectrum of a gel comprising 2% hydroxylated agarose polymer (SeaPlaque) and 1.0 mmol of 1,3-dichloropropanol in 10 ml of gelling solution.

Gels comprising agarose polymers and prepared according to the present invention have profoundly different optical properties from the agarose gels known in prior art. Fibre 5 shows a spectrum (400–800 nm) of a standard agarose gel whereas FIG. 6 shows a spectrum of the new gel containing the same agarose polymer at the same concentration. It is clear that over the whole visible spectrum new gels exhibit only a tiny fraction of the absorbance of the standard agarose gels. It has been reported that the use of derivatized agarose polymers resulted in gels with improved optical clarity (U.S. Pat. Nos. 3,956,273 and 4,319,975). A spectrum of such a gel prepared from commercial hydroxyethylated agarose polymer is shown in FIG. 7. In the visible region, the absorbance values of this gel are indeed about half of those of the standard agarose gel of the same concentration (FIG. 5), but that is still much higher than the absorbance of the gel prepared according to this invention (FIG. 6). Hydroxyethylated, agarose polymers were also used for preparation of the present gels and a spectrum of one such gel is shown in FIG. 8. Clearly, the background absorbance of this gel is almost nonexistent. It is more than one order of magnitude lower than that of the corresponding gel consisting of the same but not cross-linked hydroxyethylated agarose polymer (FIG. 7). Low background absorbance of a gel is important for a high quality recording of the separated bands. That is especially the case when separated molecules are detected without staining by means of an optical instrument, such as the one disclosed in U.S. Pat. No. 4,930,893.

The optical properties described above are more similar to synthetic gels then to standard agarose gels. Two-dimensional electrophoresis (FIG. 9) shows that in a gel comprising 1.5% agarose polymers and units derived from 1,3-dichloropropanol, 23 kbp DNA fragment migrated further than the 9.4 DNA fragment. As the same result was obtained after two-dimensional electrophoresis in a 6% poly(NAT) gels run under identical electrophoretic conditions (FIG. 2), these data indicate that the structure of the two gels is similar although their chemical composition is totally different. Thus, the change in optical properties is not merely quantitave but it reflects a profound change in gel structure.

The separation range of the new gels depended on the polymer type, its concentration, cross-linker type, cross-linker concentration as well as on the cross-linking conditions. For example, when agarose polymers were employed, a gel containing 1% polymer cross-linked with butanediol diglycidylether (0.5 ml in 20 ml) gave very good separation of DNA fragments in the size range from about 150 to 3000 bp, when electrophoresis was carried out for 1 h and 55 min at 7 V/cm. A 1.5% gel containing the same constituents (1 ml in 20 ml) and run under the same conditions gave excellent resolution in the size range from about 50 to 700 bp. When another cross-linker, 1,3-dichloropropanol, was used (1 mmol in 10 ml) then for 1% gel the separation range was from about 200 to 4000 bp. The separation range depended also on the electrophoretic conditions, primarily electric field strength and running time, as expected from published data known to those skilled in the art. Thus, when a gel comprising 1% agarose polymer and butanediol diglycidylether (0.5 ml in 20 ml) was run at a low voltage (2 V/cm) for 16 h, the separation range was from about 800 to 20000 bp.

From the way of their preparation it is clear that gels of the present invention comprise repeating units derived from the linear polysaccharide polymer and cross-linker. As noted above, the use of different cross-linkers with the same polymer resulted in gels which showed different properties regarding electrophoretic separation of biomolecules. Therefore it is likely that repeating units derived from both the polymer and cross-linker participate in selective retardation of biomolecules migrating in an electric field through a gel of the present invention. Very good resolution of small (200–600 bp) DNA fragments in present gels comprising only about 1% of agarose polymer is surprising in view of prior art but in agreement with the present model according to which gel structure is much more important than gel polymer concentration. Thus, the gel structure may be such that a low concentration of cross-linked polymers of one type gives rise to the same resistance to migrating macromolecules as a much higher concentration of cross-linked polymer of another type. Opening of "doors" and "corridors" requires a change of different magnitude in arrangement of polymer chains and the resistance they will give to these changes clearly depends on polymer type and the way the polymer chains are cross-linked.

As noted above, in many gels run in the submerged electrophoresis mode separated bands were bent. After separation of DNA fragments in gels of the present invention, some gels were cut and the shape of DNA bands examined by viewing a gel strip from its side. It was observed that the bands were bent essentially in all gels comprising more than about 2% of the polysaccharide polymer. The bending was dependent also on the gel thickness and running conditions, in general higher electric field strengths caused a more significant bending. In gels comprising agarose polymers at around 1%, the bending was negligible and it was very small at concentration of about 1.5%. Gels of these two concentrations resolve small DNA fragments very well (FIGS. 10 and 11) and therefore gels of the present invention satisfy the need for electrophoretic matrices able to resolve small biomolecules without being hampered by bending of bands.

The invention will be further illustrated by the following exemplifications, not intended as limitations unless otherwise specifically indicated herein.

EXAMPLE 1

Preparation of the branched vinyl cross-linker. The 2% aqueous agarose polymer derivatized with allylglycidylether (Acryl Aide, FMC Corporation) was warmed gently to completely dissolve the polymer. Then 12 g of the solution was transferred to a flask containing 12 g of distilled water. Under magnetic stirring, 0.220 ml of a 10 N sodium hydroxide solution was added, followed by 0.156 ml of epichlorhydrin. The flask was stoppered and the solution was vigorously stirred at room temperature for 4 h. Then, 24 ml of distilled water was added into the reaction mixture and stirring was continued for 4 days at room temperature. The resulting viscous polymer solution was extensively dialyzed, first against water and then against 30 mM Tris-acetate-EDTA buffer pH 8.0 (TAE buffer). The dialyzed solution was recovered and stored in a dark bottle at room temperature. Due to negligible dilution during the dialysis step, the polymer concentration of the cross-linked polymer solution was taken as 0.5%.

Preparation of gels. A series of poly(NAT) gels was prepared. All gels contained 6% total monomer (T) and 3% cross-linker (C). The cross-linker was either original Acryl Aide polymer or a mixture of this linear polymer and its cross-linked derivative described above. The weight sum of the two cross-linkers was always 3%. The gels (20 ml) were polymerized in 18 mM TAE buffer with TEMED (0.045 ml) and sodium persulfate (0.300 ml of a 22 mg/ml solution). The gels were fixed to Gel Bond (FMC) during polymerization. Transparency of all gels was comparable. Two sets of commercial DNA standards, 1 kbp ladder (BRL) and pBR322/Hae III (Boehringer), were run in each gel. The gels were run at 7 V/cm for 2 h and 20 min in the SEA-2000 electrophoresis apparatus (Elchrom) at 19° C. in the 30 mM TAE buffer. The apparatus is described in detail in Kozulic and Helmgartner, Analytical Biochemistry 198 (1991) 256–262. The separated DNA fragments were stained with ethidium bromide. FIG. 1 shows DNA pattern in eight different gels (a-h) with increasing concentrations of the branched cross-linker. Gel a contains no branched cross-linker, in gel b the ratio of the branched to linear cross-linker is 0.1:2.9; in gel c, 0.2:2.8; in gel d, 0.4:2.6; in gel e, 0.6:2.4; in gel f, 0.8:2.2; in gel g, 1.0:2.0 and in gel h, 1.2:1.8. As can be seen, the resolution gradually becomes worse with increasing concentrations of the branched cross-linker. The worsening occurred first in the low molecular weight range (gels d-f). At higher branched cross-linker concentrations, resolution was lost over the whole size range (gels g and h) and all DNA fragments migrated much less. It is noteworthy that other branched macromolecular cross-linkers showed the same effect. Thus, a cross-linker prepared by reacting a linear polyacrylamide polymer (MW 5,000,000, Polysciences), dissolved in ethyleneglycol, with ethylenediamine followed by dialysis and acryloylation, caused even a stronger retardation and loss of resolution in a 6% poly(NAT) gel. In some of these gels DNA molecules were not able to migrate at all.

EXAMPLE 2

Figure 2:
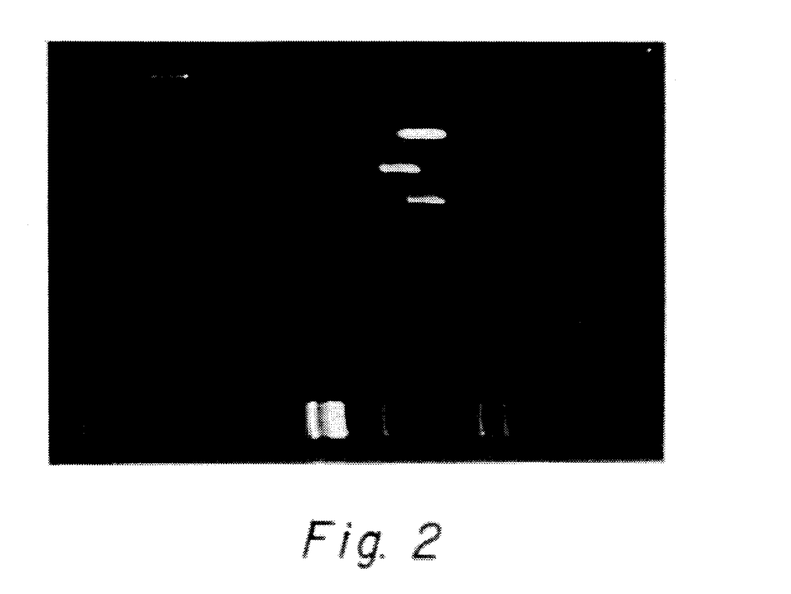
FIG. 2 shows two-dimensional electrophoresis of DNA fragments (lambda/Hind III) run in a 6% poly(NAT) gel at 2 V/cm (first dimension, top to bottom) and 7 V/cm (second dimension, left to right).

Two dimensional electrophoresis of DNA fragments in a 6% poly(NAT) gel. DNA fragments from a Lambda/Hind III digest, containing fragments of 23,130, 9,416, 6,557, 4,361, 2,322 and 2,027 bp, were resolved in the first dimension at 2 V/cm for 32 h. The running buffer was 30 mM TAE in the same submerged gel apparatus described in Example 1. After 32 h, the gel was turned by 90°. A sample containing the same fragments was applied to another sample well positioned along the other gel side and electrophoresis continued for 5 h at 7 V/cm. The gel was stained with ethidium bromide and FIG. 2 shows the pattern obtained. Electrophoresis at 2 V/cm was from top to bottom and at 7 V/cm from left to right. The 23,130 bp fragment, as the biggest one, migrated the shortest distance at 2 V/cm but at 7 V/cm it migrated further than the 9,416 bp fragment (the two top bands). It actually migrated slightly ahead of the 6,557 fragment, as can be more clearly seen in the bottom lane. Contrary to the general opinion that larger DNA fragments always migrate slower in a relatively weak homogenous electric field, FIG. 2 shows that this is not the case. It should be noted that without knowing this unexpected result, identification of bands in the lane run at 7 V/cm would be incorrect. The 2,027, 2,232 and 4,361 DNA fragments migrated in expected order and were resolved well at both electric field strengths.

EXAMPLE 3

Preparation of cross-linked agarose gels. Agarose without electroendosmosis from Serva (Cat. No. 11401) was used in all further experiments unless specified otherwise. Preparations were carried out in a fume hood due to hazardous nature of the cross-linkers. Solutions of chosen concentrations of agarose polymer were prepared in the following way. A beaker with a stirring bar was weighed and about 80% of the desired amount of water was added into it. Then the calculated amount of the agarose polymer was transferred into the beaker which was subsequently covered with a piece of Saran and placed on a heater/stirrer. The suspension was heated to boiling and left to boil until all polymer dissolved. While stirring, the solution was cooled to 65°–75° C. and then weighed again. The remaining amount of water, to make the desired concentration, was then added followed by cross-linking reactants. When the volume of these reactants represented more than about 5% of volume of the agarose solution, then correspondingly less water was added.

A 1% agarose solution (72 ml) was prepared as described above and 0.660 ml of 10N NaOH was added under stirring. Three 12 g aliquotes of this solution were taken and poured into gel molds. To the remaining solution 0.234 ml of epichlorhydrin was added and the solution vigorously stirred for about 2–3 min. The solution was transferred to other three gel molds. Two of each gel molds, one with and the other without epichlorhydrin, were placed in closed polypropylene boxes with enough water to keep the atmosphere saturated with water vapor. The boxes were placed into incubators at 45°, 55° and 65° C. The gel molds were made of polymethylmethacrylate and contained sample well formers. The gel dimensions were 92×62 mm and they were 1.5 mm thick. The gels were fixed onto a piece of Gel Bond (for agarose gels, FMC) during gel formation.

After an overnight incubation at the above specified temperatures, the gels were inspected. No handleable gel formed from solutions without epichlorhydrin at either of the three temperatures. In contrast, gels that stuck strongly to the plastic support were formed at all three temperatures from solutions containing epichlorhydrin. All three gels were fully transparent. The gels were soaked in distilled water, three one-liter changes within eight hours, and then in 30 mM TAE buffer overnight. Two different DNA standards were electrophoresed in each gel. DNA fragments were from the 1 kb ladder (BRL) with the following sizes: 12216, 11198, 10180, 9162, 8144, 7126, 6108, 5090, 4072, 3054, 2036, 1636, 1018, 516, 506, 396, 344, 298, 220, 201, 154, 134 and 75 base pairs. Another sample included fragments from pBR322/Hae III (Boehringer) with sizes 587, 540, 504, 458, 267, 234, 213, 192, 184, 124, 123, 104, 89, 80, 64, 57 and 51 bp. The gels were run at 7 V/cm for 1 hour and 50 min and then stained with ethidium bromide.

Figure 3:
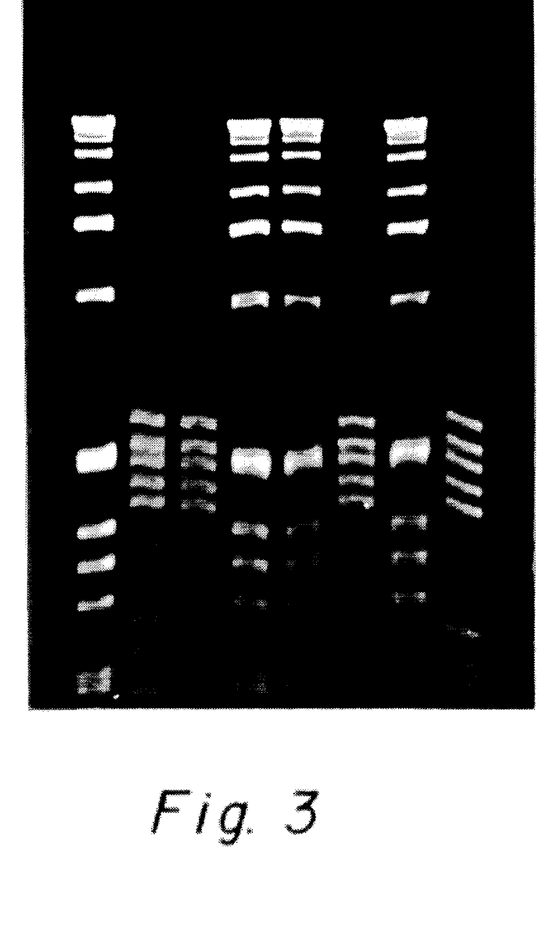
FIG. 3 shows resolution of DNA fragments (1 kbp ladder and pBR322/Hae III) resolved in a 1% agarose gel cross-linked with epichlorhydrin at 65° C.
Figure 4:
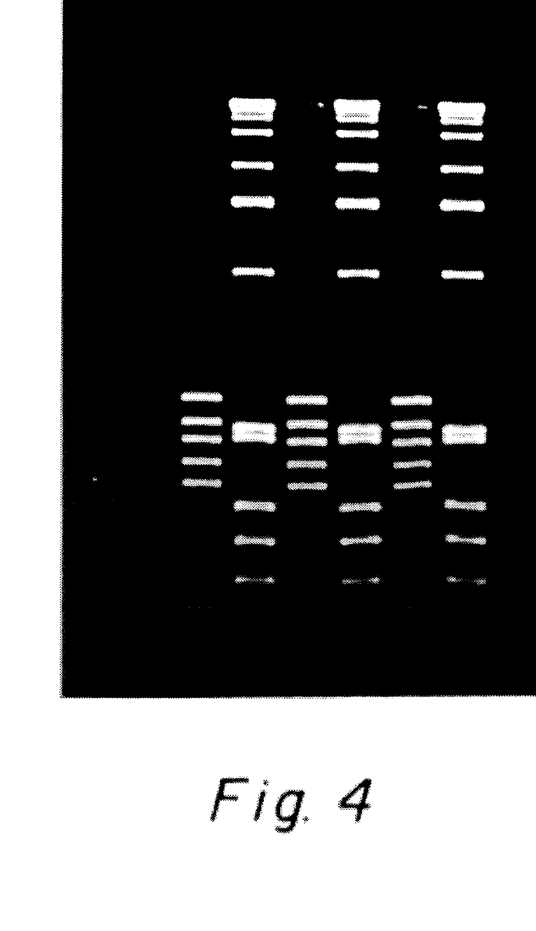
FIG. 4 shows the same DNA fragments as in FIG. 3 but resolved in a gel cross-linked at 45° C.

FIG. 3 shows DNA pattern in the gel incubated at 65° C. Resolution in the whole size range is poor. The gel incubated at 55° C. shows somewhat better resolution (not shown). Resolution over the whole size range is much better in the gel incubated at 45° C. (FIG. 4).

EXAMPLE 4

Gels prepared by cross-linking agarose polymers with different concentrations of epichlorhydrin. Agarose with electroendosmosis (SeaKern GT grade, FMC) was used. Into a 1% agarose solution (40 ml) epichlorhydrin and sodium hydroxide (10N solution) were added at such a ratio that there was always 1.1 molar excess of sodium hydroxide. The final quantities of epichlorhydrin were 0, 1, 2, 4, 4, 6 and 10 mmol. The gels were 3 mm thick and were left overnight at room temperature. Transparency of gels improved with increasing cross-linker concentrations. After washing with water and equilibration against the TAE buffer, as described in Example 3, DNA fragments were analyzed in these gels. In the gel without any cross-linker, there was no resolution between 517 and 506, between 220 and 201 and between 154 and 134 bp fragments from the 1 kbp ladder. There was only a slight difference in band pattern in the gels cross-linked with 1, 2 and 4 mmol of the cross-linker. However, in the gel cross-linked with 6 mmol the above three doublets were partially resolved and in the gel cross-linked with 10 mmol of epichlorhydrin they were fully resolved. The migration distances were also much shorter in the last two gels, so that the 75 bp fragment did not migrate out of these gels. These results indicate that quality of resolution depends on the polymer/cross-linker ratio. The above gels as well as others comprising less than about 2% polymer could be dried, in the open air, to a thin film without curling of the plastic support. The dried gels rehydrated when placed into water and the rehydration degree was dependent on the polymer and cross-linker type and quantity.

EXAMPLE 5

Gels comprising agarose and epichlorhydrin prepared by incubating the reaction mixture at different temperatures for different time. The gels contained 0.6 g of agarose (FMC, GT grade), 0.780 ml of epichlorhydrin and 1 ml of 10N NaOH in 40 ml. After pouring the solution into gel molds, the first gel was incubated at room temperature overnight, the second at 35° C. from three days, the third at 45° C. overnight and the fourth initially at 4° C. overnight and then two days at room temperature. The gels were washed and equilibrated as described above. Various DNA fragments were electrophoresed in these gels at 7 V/cm for one hour and 45 min. After staining with ethidium bromide very sharp bands were observed in the first three gels, whereas the bands were less sharp in the fourth gel. The 587 bp fragment from pBr322/Hae III migrated the shortest distance in the fourth gel and essentially the same distance in the first and second gel. The 123/124 bp fragments migrated essentially equal distance in all gels. The 184 and 192 bp fragments were resolved in all gels, however, resolution was the best in the second gel.

Another two gels of the same composition were prepared and incubated at room temperature overnight, but one gel was additionally incubated at 45° C. for two days. Electrophoresis was at 7 V/cm for 2 hours and 30 min. Sharp bands were observed in both gels. All DNA bands migrated less in the gel which was additionally incubated at 45° C. These results demonstrate that quality of resolution can be controlled by varying temperature and time of gel formation. A piece (about 1×1 cm) of the second gel was heated in boiling water. The gel did not dissolve.

EXAMPLE 6

Gels comprising agarose and butanediol diglycidylether prepared at different polymer/cross-linker ratios and incubated for different time periods at various temperatures. Gels (1.5 mm thick) were prepared from 10 ml of 1% agarose solution which was made 0.1M in NaOH and contained 0.05, 0.1, 0.2, 0.4, 0.6 ml butanediol diglycidylether. The molds with the above reaction mixtures were incubated at room temperature for 4 days. After electrophoresis (7 V/cm, 1 h 50 min), it was observed that the migration distances of DNA fragments decreased with the increase of the butanediol diglycidylether concentration. The resolution was also better at higher concentrations of the cross-linking reagent. In the next experiment a series of 1% agarose gels, containing 0.1M NaOH and 0.5 ml of butanediol diglycidylether in 20 ml, was incubated at room temperature for 16 and 24 h and 2, 4 and 5 days. Electrophoresis of DNA fragments showed poor resolution in the gel incubated for 16 h. With longer incubations migration distances became shorter and resolution was improved. There was essentially no difference between the gels incubated for 4 and 5 days. Proteins (ferritin and thyroglobulin) were applied into some sample wells of these gels and electrophoresed at the same time with DNA. At the end of the run, the gel was cut and the part containing proteins stained with Coomassie Blue. Thyroglobulin migrated less, relative to ferritin, in the gels incubated for 4 and 5 than 1 day.

Figure 10:
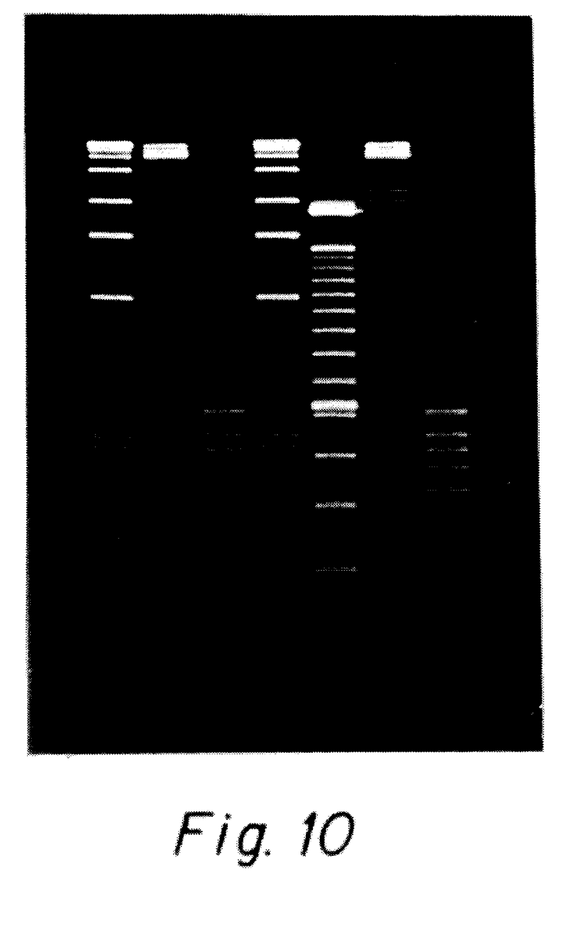
FIG. 10 shows separation of various DNA fragments in a gel comprising 1% agarose polymer and 0.5 ml of butanediol diglycidylether in 20 ml of gelling solution.
Figure 11:
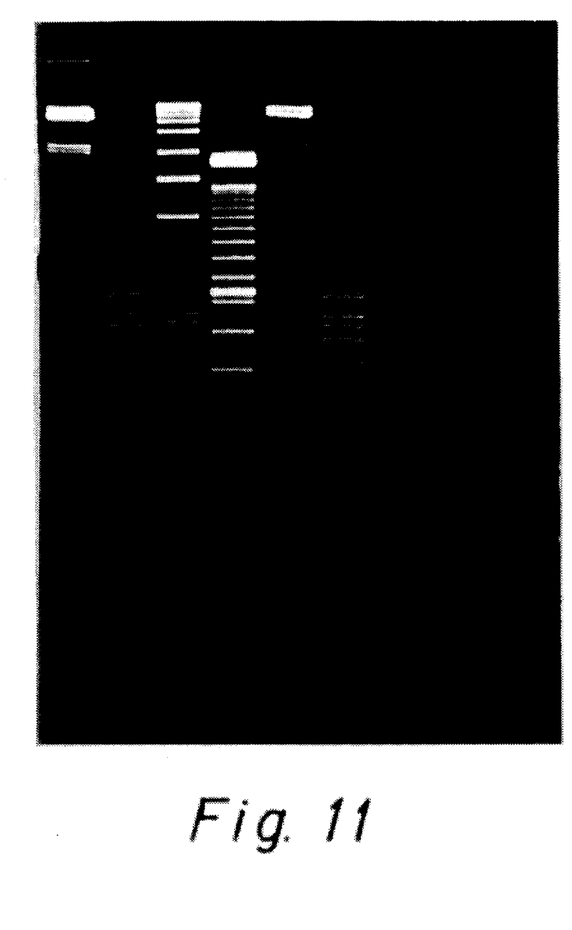
FIG. 11 shows separation of various DNA fragments in a gel comprising 1.5% agarose polymer and 1 ml of butanediol diglycidylether in 20 ml of gelling solution.

Three gels, comprising 1% agarose solution in 0.1M NaOH and 0.5 ml of butanediol diglycidylether in 20 ml, were formed by incubation for 2 days at 35°, 55° or 65° C. Resolution of DNA fragments, especially of the small ones, was poor in the gel incubated at 65° C. but it was excellent in the gel incubated at 35° C. (FIG. 10). The resolution was also excellent in another gel, comprising 1.5% agarose and formed by incubated 20 ml of agarose solution in 0.1M NaOH with 1 ml of the cross-linker at 35° C. for 2 days, but the separation range was different (FIG. 11). Thus, the 123 bp fragment migrated out of the 1% gel but it was more than 1.5 cm far from the bottom of the 1.5% gel. Resolution of DNA fragments above about 500 bp was better in the 1% gel and resolution of smaller fragments was better in the 1.5% gel.

EXAMPLE 7

Gels comprising agarose and 1,3-dichloropropanol prepared at different polymer/cross-linker ratios and incubated for different time periods. A series of gels was prepared comprising 1% agarose polymer and with it dissolved in 10 ml 0.25, 0.5, 1.0, 1.5, 2.0 and 2.5 mmol of 1,3-dichloropropanol (DCP) and 0.55, 1.1, 2.2, 3.3, 4.4 and 5.5 mmol of sodium hydroxide, respectively. Thus there was always a molar excess (10%) of hydroxide over chloride. The solutions were poured into gel molds and incubated at 35° C. for 2 days. Electrophoresis of DNA at 7 V/cm for 1 hour and 50 min showed differences in migration distances and resolution of DNA fragments. Thus, the 267 bp fragment (from pBR322/Hae III) was just at the bottom of the gel cross-linked with 0.25 mmol DCP, whereas it was more than 1 cm away from the bottom of the gel cross-linked with 2.5 mmol DCP.

Another series of gels was made by preparing a 1.5% solution of agarose in water and adding 1,3-dichloropropanol (1, 2, 3 and 4 mmol) and 10N NaOH (2.2, 4.4, 6.6 and 8.8 mmol) to 10 ml of the warm agarose solution. The gelling was for 4 days at 35° C. Electrophoresis of DNA fragments resulted in sharper bands in the gels with 2 and 3 than in the gel with 1 mmol of 1,3-dichloropropanol. It is noteworthy that the larger DNA fragments, above 500 bp, migrated further in the gel with 4 mmol than in the gel with 3 mmol of the cross-linker. Relative to ferritin, thyroglobulin migrated further in the gel with 4 mmol cross-linker. In addition, that gel was also softer than the gels with less cross-linker. Thus, there is an optimal cross-linker concentration and exceeding it may worsen not only resolution but also mechanical stability.

A series of gels containing 2% of agarose polymers and 0, 0.1, 0.2, 0.4, 0.6, 1.0, 2.0 and 4.0 mmol of 1,3-dichloropropanol, plus NaOH in 10% molar excess over chlorine, in 10 ml were prepared by incubation at 35° C. for 4 days. A portion of about 1.5 ml of each gel solution (in triplicate) was placed in polystyrene cuvettes, overlaid with paraffin oil and incubated under the same conditions. Electrophoresis of DNA fragments (7 V/cm, 1 h 50 min) showed improved resolution of DNA fragments below 1000 bp with increasing cross-linker concentration to about 1 mmol and remained good to 4.0 mmol. Transparency of the gels was determined by measuring the absorbance at 500 nm (Table 1) and recording a visible spectrum (400–800 nm) of the gels equilibrated at room temperature overnight. The spectrum of the agarose gel comprising no cross-linker is shown in FIG. 5. The absorbance values at all wavelengths decreased with increasing cross-linker concentrations and became essentially constant beyond 1 mmol. The visible spectrum of the gel prepared with 2 mmol of 1,3-dichloropropanol in 10 ml is shown in FIG. 6. The absorbance at 500 nm of this gel is over one order of magnitude lower than that of the standard agarose gel (Table 1). The UV spectrum, recorded after transferring a gel into a quartz cuvette, showed a low absorbance in the 300–400 nm region, a shoulder around 260 nm a steep rise below about 230 nm.

Figure 9:
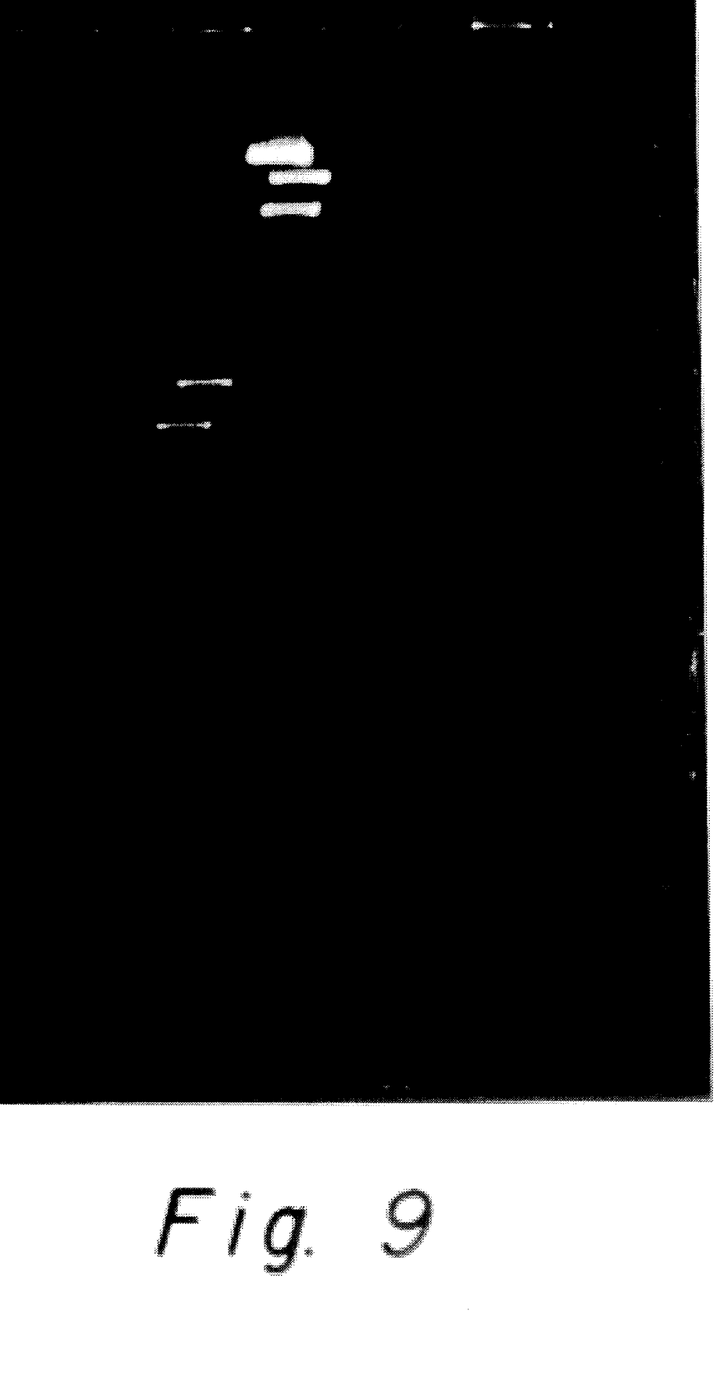
FIG. 9 shows two-dimensional electrophoresis of DNA fragments (lambda/Hind III) in a gel comprising 1.5% agarose polymers and units derived from 1,3-dichloropropanol run at 2 V/cm (first dimension, top to bottom) and 7 V/cm (second dimension, right to left).

Two dimensional electrophoresis of lambda/Hind III fragments was carried out in a gel comprising 1.5% agarose polymer cross-linked with 1,3-dichloropropanol at 1.5 mmol per 10 mi. In the first dimension the gel was run at 2 V/cm for 16 h. After turning the gel by 90° the second dimension electrophoresis was carried out at 7 V/cm for 4 h. FIG. 9 shows that at 7 V/cm the 23 kbp fragment migrated further than the 9.4 kbp fragment. Since this result is the same as that shown in FIG. 2, it indicates that the mechanism of DNA migration in both gels is identical.

EXAMPLE 8

Gels comprising hydroxyethylated agarose and 1,3-dichloropropanol at different polymer/cross-linker ratios. A series of gels comprising 2% hydroxylated agarose polymer (SeaPlaque, FMC) and the cross-linker was prepared in the way described in Example 7. Electrophoresis of DNA fragments showed improved resolution, clearly visible already at the lowest cross-linker concentration, with respect to the standard gel. Measurement of absorbance at 500 nm demonstrated essentially no change at cross-linker concentration above 0.6 mmol in 10 ml. A visible spectrum of the standard SeaPlaque gel is shown in FIG. 7. FIG. 8 shows the spectrum of the gel comprising hydroxylated agarose polymer and 1.0 mmol of 1,3-dichloropropanol in 10 ml. The gel comprising hydroxylated agarose displays about one half of absorbance of the underivatized agarose in the visible region (compare FIG. 5 and FIG. 7). On the other hand, the present gels which in addition to the same polymers comprise a cross-linker, showed less than one tenth of absorbance of the gels with no cross-linker. Actually, the absorbance of the present gels comprising hydroxylated agarose and higher amounts of the cross-linker is almost nonexistent in the visible region (FIG. 8).

EXAMPLE 9

Gels comprising agarose and 2,3-dibromopropanol prepared at different polymer/cross-linker ratios. A series of gels comprising 1% agarose polymer and 0.25, 0.5, 1.0, 1.5, 2.0 and 2.5 mmol of 2,3-dibromopropanol in 10 ml was prepared. The gel solution included also sodium hydroxide in 10% molar excess over bromide. The gels were incubated at 35° C. for two days. Electrophoresis of DNA fragments showed improved resolution in the small molecular weight range, especially at 1–2 mmol of the cross-linker. The resolution was somewhat inferior to that achieved with gels cross-linked wit 1,3-dichloropropanol. Occasionally, small bubbles could be noticed in the gels.

EXAMPLE 10

Gels comprising agarose and ethyleneglycol diglycidylether prepared at different polymer/cross-linker ratios. A series of gel comprising 1% agarose polymer in 0.1 M NaOH and 0.05, 0.1, 0.2, 0.4 and 0.6 ml of ethyleneglycol diglycidylether in 10 ml was prepared by incubation at room temperature for 4 days. Electrophoresis showed reduced migration distances with increasing cross-linker concentration. Resolution was inferior to that obtained with butanediol diglycidylether.

EXAMPLE 11

Gels comprising agarose and dimylsulfone prepared at different polymer/cross-linker ratios at various pH values for different time. Into a warm 1% agarose solution in 0.1M NaOH, 0.010 ml of divinylsulfone was added under rapid stirring. The solution was immediately transferred into a gel mode. The gel solidified within minutes. The solidification was faster at higher cross-linker concentrations which made it practically impossible to reproducible prepare such gels. Electrophoresis showed a pronounced decrease in migration distances related to those in the standard gel.

Agarose solutions (1%) were prepared in 0.2M bicarbonate-carbonate buffers with pH 8, 9.5 and 11.0. To 20 ml of each of these solutions 0.1 ml of divinylsulfone was added and the gel solutions incubated at 35° C. for 2 days. DNA fragments migrated less and appeared as sharper bands in the gel formed at pH 8 than at pH 9.5. In the gel formed at pH 11 the fragments migrated less that in either of the two gels. The bands corresponding to small DNA fragments were the sharpest in this gel.

A series of gels was prepared which comprised 1% agarose in 10 mM NaOH and 0.020, 0.040, 0.060, 0.080 and 0.100 ml of divinylsulfone per 20 ml. After addition of the cross-linker each gel was immediately poured in the gel mold and left there for 15 min. The gel with 0.100 ml of the cross-linker was too weak for subsequent handling. The other gels were washed in water and equilibrated in the TAE buffer. Electrophoresis showed decreased migration distances with increasing cross-linker concentrations. The DNA bands in all four gels were more diffuse than in the above gel cross-linked at pH 11 for 2 days.

EXAMPLE 12

Gels comprising agarose and butanediol diglycidylether by addition of the cross-linking reagent to the polymer solutions at different temperatures. To 1% solution of agarose in 0.1M NaOH the cross-linker was added (0.5 ml per 20 ml) at 50° and 70° C. under vigorous stirring. The gel solutions were immediately poured in the gel molds and incubated at 35° C. for three days. Electrophoresis of DNA fragments in the three gels showed essentially the same result, that is the migration distances did not differ more than 1–2 mm after running the gels at 7 V/cm for 1 h and 50 min. A similar result was obtained with 1,3-dichloropropanol as the cross-linker.

EXAMPLE 13

Gels comprising hydroxyethylcellulose and butanediol diglycidyl ether. A 5% solution of hydroxyethylcellulose (Fluka, Cat. No. 54290) was prepared in 0.1M NaOH by prolonged stirring (1–2 days). To 10 ml of this solution 0.5 ml of butanediol diglycidylether was added under stirring and the solution incubated at room temperature for three days. Another gel was prepared by diluting the polymer solution with 0.1M NaOH to 4% and adding the same amount of the cross-linker. Fully transparent gels of good mechanical stability were formed from both solutions. Following washing and equilibration, electrophoresis of DNA fragments showed very sharp bands and good resolution of DNA fragments in the size range from 75 to 2000 bp in the 4% gel. All fragments migrated much less in the 5% gel and the resolution was not as good as in the 4% gel. In some similar gels incubated at 35° C. small bubbles were occasionally observed, probably caused by gel shrinkage.

EXAMPLE 14

Gels comprising dextran and butanediol diglycidylether. Solutions (6, 8 and 10%) of dextran (Fluka, Cat. No. 31392) in 0.1M NaOH were prepared and to 20 ml of each of these solutions 0.5 ml of the cross-linker was added. The solutions were incubated at room temperature for three days. During washing in water and equilibration in the TAE buffer it was observed that the all gels swelled. The swelling was accompanied by distortion of sample wells which almost closed, making sample application difficult. Electrophoresis of DNA fragments showed moderate resolution in the 6% gel and very poor resolution in the 8 and 10% gels. In all gels the shape of DNA bands was crescent.

EXAMPLE 15

Attempted preparation of gels comprising starch and butanediol diglycidylether. A 2% solution of starch (Fluka, Cat. No. 85645) was prepared in 0.1M NaOH and 0.5, 1.0 and 1.5 ml of the cross-linker added per 20 ml of the polymer solution. No manageable gel formed after incubation at 35° C. for two days.

EXAMPLE 16

Gels comprising agarose, butanediol diglycidylether or 1,3-dichloropropanol and additional polymers comprising hydroxyethyl cellulose, polyvinyl alcohol, starch and dextran. A solution of 1% agarose polymers and 0.5% of starch was prepared in 0.1M NaOH and to 20 ml of this solution 0.5 ml of butanediol diglycidylether was added. A gel which formed after incubation at 35° C. for 2 days showed very good resolution of DNA fragments in the 100–2000 bp range. Another gel was prepared under identical conditions but it contained 0.5% dextran instead of starch. The separation range was the same but DNA bands were less sharp than in the gel comprising starch. A gel comprising 0.5% hydroxyethylcellulose and 1% agarose polymers was also prepared by incubation for 1 day at 35° C. Resolution of DNA fragments was very good and the 104 bp fragment migrated about 0.5 cm less than in the gel comprising starch. Two gels comprising polyvinylalcohol, 0.5 and 1%, in addition to 1% agarose polymers were prepared in the same way. The gel which comprised 0.5% of polyvinylalcohol showed sharper bands and very good resolution in the size range from 120 to 3000 bp.

Gels were also prepared in which the order of reagent addition was changed. Thus, one gel was prepared by adding 2.5 mmol of 1,3-dichloropropanol to a solution of agarose and hydroxyethylcellulose (10 ml, both polymers at 1%) and the other by adding 2.5 mmol of 1,3-dichloropropanol to a solution of agarose followed by addition of hydroxyethylcellulose. The final concentration of each polymer was 1%. The solutions contained 5 mmol of NaOH before addition of the cross-linker. Following incubation at 35° C. for two days, electrophoresis of DNA fragments showed essentially no difference in migration distances between identical DNA fragments run in the two gels.

EXAMPLE 17

Gels comprising agarose and epichlorhydrin prepared by dilution of the cross-linker prior to its addition into the polymer solution. Dioxane (1 ml) was used to dilute the cross-linker (1 mmol) before it was added to 9 ml of 1.1% agarose solution containing 1.1 mmol of NaOH. The gel solution was incubated at 35° C. for two days. Following washing and equilibration, electrophoresis showed very good resolution of DNA fragments.

TABLE 1

Absorbance at 500 nm of gels comprising 2% agarose polymers cross-linked with different amounts of 1,3-dichloropropanol (mmol in 10 ml of gel) prepared as described in Example 7.

| mmol | 0.0 | 0.1 | 0.2 | 0.4 | 0.6 | 1.0 | 2.0 | 4.0 |
|---|---|---|---|---|---|---|---|---|
| $A_{500}$ | 0.396 | 0.191 | 0.128 | 0.058 | 0.024 | 0.028 | 0.027 | 0.040 |

While this invention has been illustrated and described by the specific figures and examples, it is recognized that variations and changes may be made without departing from the invention as set forth in the claims.

What is claimed is:

1. A substantially continuous bed of a substantially water insoluble, substantially transparent, substantially uniform composition gel comprising a gelled, ether cross-linked reaction product of a quiescent composition comprising a solution comprising a linear polysaccharide and a cross-linking agent, wherein said agent comprises a compound which is substantially devoid of functional groups which are charged, or which become charged upon contact with water, in a pH range of about 2 to 11 and which reacts with said polysaccharide to form ether linkages therewith, wherein said cross-linked reaction product gel has a sufficiently low charge that it does not interfere with the use of said gel in submerged electrophoresis, and wherein said cross-linked reaction product gel was made by substantially simultaneous cross-linking and gelation.

2. A bed of crosslinked gel as claimed in claim 1, wherein said crosslinking agent is hydrophilic and reacts with water to form an alcohol.

3. A bed of cross linked gel as claimed in claim 1 which is soft and elastic.

4. A gel of claim 1, wherein the linear polysaccharide is agarose.

5. A gel of claim 1, wherein the linear polysaccharide is hydroxyethyl cellulose.

6. A gel of claim 1, wherein the linear polysaccharide is hydroxyethyl agarose.

7. A gel of claim 1 comprising a linear polysaccharide and at least one additional polysaccharide.

8. A gel of claim 7, comprising linear polysaccharide is agarose and the branched polysacharide is dextran.

9. A gel of claim 7, comprising the linear polysaccharide is agarose and the branched polysaccharide is starch.

10. A gel of claim 1 wherein said linear polysaccharide comprises agarose and hydroxyethyl cellulose.

11. A gel according to claim 1 comprising at least one synthetic polymer with hydroxyl groups and said linear polysaccharide.

12. A gel of claim 11, wherein the synthetic polymer is polyvinyl alcohol.

13. A gel according to claim 1 wherein the cross-linker is at least one member selected from a group of compounds consisting of dihaloalkyl alcohols, halohydrins, bisepoxides, divinyl sulfone, alkanediol dialkyl sulfonates, and alkanediol diaryl sulfonates.

14. A gel of claim 13, wherein substantially simultaneous cross-linker reaction and gel formation is carried out at pH values from 8 to 14.

15. A gel of claim 13, wherein substantially simultaneous cross-linker reaction and gel formation is carried out at temperatures from 4° to 65° C.

16. A gel of claim 13, wherein substantially simultaneous cross-linker reaction and gel formation is carried out for periods varying from 15 minutes to 5 days.

17. A gel according to claim 13, wherein the cross-linker reaction and gel formation is carried out in water as solvent.

18. A gel according to claim 13, wherein the cross-linker reaction and gel formation is carried out in a water-organic solvent mixture.

19. The combination of a gel according to claim 1 and a support fixed thereto.

20. The combination claimed in claim 19 made by a process in which, during said substantially simultaneous cross-linking reaction and gelation, said solution of said polysaccharide is in effective contact with said supporting article having at least one surface to which said gel becomes affixed.

21. The gel as claimed in claim 1 which is substantially uncharged.

* * * * *